United States Patent
Van Zee

(10) Patent No.: US 10,834,884 B2
(45) Date of Patent: Nov. 17, 2020

(54) LETTUCE VARIETY NUN 09094 LTL

(71) Applicant: NUNHEMS B.V., Nunhem (NL)

(72) Inventor: Johan Van Zee, Nunhem (NL)

(73) Assignee: NUNHEMS B.V., Nunhem (NL)

( * ) Notice: Subject to any disclaimer, the term of this patent is extended or adjusted under 35 U.S.C. 154(b) by 108 days.

(21) Appl. No.: 16/003,890

(22) Filed: Jun. 8, 2018

(65) Prior Publication Data

US 2018/0288959 A1   Oct. 11, 2018

Related U.S. Application Data

(60) Provisional application No. 62/517,218, filed on Jun. 9, 2017.

(51) Int. Cl.
*A01H 6/14* (2018.01)
*A01H 5/12* (2018.01)

(52) U.S. Cl.
CPC ............ *A01H 6/1472* (2018.05); *A01H 5/12* (2013.01)

(58) Field of Classification Search
None
See application file for complete search history.

(56) References Cited

U.S. PATENT DOCUMENTS

| | | | |
|---|---|---|---|
| 9,756,829 B2 * | 9/2017 | van Zee | A01H 5/12 |
| 2008/0222949 A1 | 9/2008 | Bissonnette et al. | |
| 2016/0316709 A1 * | 11/2016 | van Zee | A01H 5/12 |
| 2018/0359979 A1 * | 12/2018 | Van Zee | A01H 5/12 |

FOREIGN PATENT DOCUMENTS

| | | |
|---|---|---|
| EP | 1197137 A1 | 4/2002 |
| WO | 2013182646 A1 | 12/2013 |

OTHER PUBLICATIONS

"Guidelines for the conduct of tests for distinctness, uniformity and stability", UPOV (International Union for the Protection of New Varieties and Plants) http://www.upov.int/edocs/tgdocs/en/tg013.pdf (Apr. 5, 2017).
"Objective description of Variety—Lettuce (*Lactuca sativa* L.)", U.S. Department of Agriculture, Agricultural Marketing Service, Science and Technology, Plant Variety Protection Office, Beltsville, MD 20705 http://www.upov.int/export/sites/upov/meetings/en/2013/EAF_1/US_PVP_06.pdf.
Teng et al., "Rapid Regeneration of Lettuce from Suspension Culture", HortScience, vol. 27(9), pp. 1030-1032, (1992).
Teng et al., "Regenerating Lettuce from Suspension Culture in a 2-Liter Bioreactor", HortScience, vol. 28(6), pp. 669-671, (1993).
Zhang et al., "Genotypic effects on tissue culture response of lettuce cotyledons", Journal of Genetics and Breeding, vol. 46, No. 3, pp. 287-290, (1992).
Gonai et al., "Abscisic acid in the thermoinhibition of lettuce seed germination and enhancement of its catabolism by gibberellin", Journal of Experimental Botany, vol. 55, No. 394, pp. 111-118, (Jan. 2004).
Brotman et al., "Resistance gene homologues in melon are linked to genetic loci conferring disease and pest resistance", Theor Appl Genet, vol. 104, pp. 1055-1063, (2002).
Clewer, A. G., and D. H. Scarisbrick, "Practical Statistics and Experimental Design for Plant and Crop Science", Wiley (2001).
Allard, Robert W., "Principles of Plant Breeding," Second Edition, pp. 119-128, (1999).

\* cited by examiner

*Primary Examiner* — Soren Harward
*Assistant Examiner* — Wayne Zhong
(74) *Attorney, Agent, or Firm* — Arent Fox LLP

(57) ABSTRACT

The disclosure relates to lettuce variety NUN 09094 LTL as well as seeds and plants and heads or leaves thereof.

26 Claims, No Drawings

US 10,834,884 B2

LETTUCE VARIETY NUN 09094 LTL

CROSS-REFERENCE TO RELATED APPLICATIONS

The application claims the benefit of U.S. Patent Application Ser. No. 62/517,218, filed Jun. 9, 2017, which is incorporated herein by reference in its entirety.

FIELD OF THE INVENTION

The disclosure relates to the field of plant breeding and, more specifically, to the development of NUN 09094 LTL. The disclosure further relates to vegetative reproductions of NUN 09094 LTL, methods for in vitro tissue culture of NUN 09094 LTL, an explant and also to phenotypic variants of NUN 09094 LTL.

BACKGROUND

The goal of plant breeding is to combine various desirable traits in a single variety. Such desirable traits may include greater yield, resistance to diseases, insects or other pests, tolerance to heat and drought, better agronomic quality, higher nutritional value, enhanced growth rate and improved shelf life.

The development of commercial lettuce cultivars or varieties requires the crossing of lettuce plants, and the evaluation of the crosses. Pedigree breeding and recurrent selection are examples of breeding methods are used to develop cultivars from breeding populations. Breeding programs combine desirable traits from two or more varieties or various broad-based sources into breeding pools from which cultivars are developed by selfing and selection of desired phenotypes. The new cultivars are crossed with other varieties and the inbred lines or hybrids from these crosses are evaluated to determine which have commercial potential.

All cultivated forms of lettuce belong to the highly polymorphic species *Lactuca sativa* that is grown for its edible head and leaves. *Lactuca sativa* is in the Asteraceae (Compositae) family. Lettuce is related to chicory, sunflower, aster, dandelion, artichoke and chrysanthemum. *L. sativa* is one of about 300 species in the genus *Lactuca*. There are many types of lettuce, and new types are constantly in development. Types of lettuce include Cutting/Leaf, Iceberg/Crisphead, Cos or Romaine, Batavian, Salinas Group, Latin, Butterhead, Great Lakes Group, Eastern (Ithaca) Group, Bibb, Vanguard Group, multileaf or Stem lettuce.

Fresh lettuce is available in the United States year-round although the greatest supply is from May through October. For planting purposes, the lettuce season is typically divided into three categories, early, mid and late, with the coastal areas planting from January to August, and the desert regions planting from August to December. Lettuce is consumed nearly exclusively as fresh, raw product and occasionally as a cooked vegetable.

Lifestyles change and the demand from restaurants and catering firms for colorful and interesting garnish for sandwiches and ready-to-use processed salads continue to rise. As a result, there is a demand for breeding companies to develop new varieties with specific shapes of leaves, specific average size of leaves, glossiness, prominent color and a wide variety of texture, as well as good yield.

SUMMARY OF VARIOUS EMBODIMENTS OF THE INVENTION

The disclosure provides for lettuce variety NUN 09094 LTL, products thereof, and methods of using the same. NUN 09094 LTL is a narrow oakleaf lettuce that can be grown as babyleaf, and is suitable for growing in the open field.

In one aspect, the disclosure provides a seed of lettuce variety NUN 09094 LTL, wherein a representative sample of said seed will be deposited under Accession No. NCIMB 43664. The disclosure also provides for a plurality of seeds of NUN 09094 LTL. The seed of NUN 09094 LTL may be provided as an essentially homogeneous population of lettuce seed. The population of seed of NUN 09094 LTL may be particularly defined as essentially free from other seed. The seed population may be grown into plants to provide an essentially homogeneous population of lettuce plants described herein.

The disclosure also provides a plant grown from a seed of lettuce variety NUN 09094 LTL and a plant part thereof. In another aspect, the disclosure provides for an inbred lettuce variety NUN 09094 LTL. The disclosure also provides for a progeny of NUN 09094 LTL. In another aspect, the disclosure also provides a plant or a progeny retaining all or all but one, two or three of the "distinguishing characteristics" or all or all but one, two or three of the "morphological and physiological characteristics" of NUN 09094 LTL, and methods for producing that plant or progeny.

In one aspect, the disclosure provides a plant or a progeny having all the physiological and morphological characteristics of NUN 09094 LTL when grown under the same environmental conditions. In another aspect, the plant or progeny has all or all but one, two or three of the physiological and morphological characteristics of NUN 09094 LTL, when measured under the same environmental conditions and evaluated at significance levels of 1%, 5% or 10% significance (which can also be expressed as a p-value), wherein a representative sample of seed of NUN 09094 LTL will be deposited under Accession No. NCIMB 43664. In another aspect, the plant or progeny has all or all but one, two or three of the physiological and morphological characteristics as listed in Table 1 and/or 2 for NUN 09094 LTL when measured under the same environmental conditions and evaluated at significance levels of 1%, 5% or 10% significance (which can also be expressed as a p-value).

In another aspect a plant of NUN 09094 LTL or a progeny thereof has 7, 8, or more or all of the following distinguishing characteristics: 1) Average mature leaf length; 2) Average mature leaf width; 3) Typical mature leaf margin incision density; 4) Typical mature leaf margin indentation; 5) Typical mature leaf undulation of the apical margin; 6) Typical mature leaf blistering; 7) Typical mature leaf thickness; 8) Average mature plant spread of frame leaves; 9) Average core diameter at base of head; and 10) Ratio of frame leaves/core diameter.

The disclosure provides for a plant part obtained from NUN 09094 LTL, wherein said plant part is: a leaf, a part of a leaf, a head, a part of a head, a fruit, a part of a fruit, pollen, an ovule, a cell, a petiole, a shoot or a part thereof, a stem or a part thereof, a root or a part thereof, a root tip, a cutting, a seed, a part of a seed, seedcoat or another maternal tissue which is part of a seed grown on said variety, hypocotyl, cotyledon, a pistil, an anther, or a flower or a part thereof. Heads and leaves are particularly important plant parts. In yet another aspect, the disclosure provides a seed of NUN 09094 LTL. In still another aspect, the disclosure provides a seed growing or grown on a plant of NUN 09094 LTL. In another aspect, the plant part obtained from NUN 09094 LTL is a cell, optionally a cell in a cell or tissue culture. That cell may be grown into a plant of NUN 09094 LTL.

The disclosure also provides a cell culture of NUN 09094 LTL and a plant regenerated from NUN 09094 LTL, which plant has all the characteristics of NUN 09094 LTL when grown under the same environmental conditions, as well as methods for regenerating NUN 09094 LTL. Alternatively, a regenerated plant may have one characteristic that is different from NUN 09094 LTL.

The disclosure further provides a vegetatively propagated plant of NUN 09094 LTL having all or all but one, two or three of the morphological and physiological characteristics NUN 09094 LTL when grown under the same environmental conditions.

The disclosure also provides a lettuce head and/or a lettuce leaf produced on a plant grown from a seed of NUN 09094 LTL.

In another aspect, the disclosure provides a seed growing or grown on a plant of NUN 09094 LTL (i.e., produced after pollination of the flower of NUN 09094 LTL). The disclosure further provides an F1 progeny of NUN 09094 LTL.

Definitions

"Lettuce" refers herein to plants of the species *Lactuca sativa* L. The most commonly eaten parts of a lettuce plant are the head or a leaf. The head comprises a core and leaves, which may be divided in inner and outer leaves.

"Cultivated lettuce" refers to plants of *Lactuca sativa* (e.g., varieties, breeding lines or cultivars of the species *L. sativa* as well as crossbreds thereof, or crossbreds with other *Lactuca sativa* species, or even with other *Lactuca* species), cultivated by humans and having good agronomic characteristics.

"Leaf lettuce" or "cutting lettuce" refers to a type of lettuce with very loose leaves, that does not form a head.

The terms "NUN 09094 LTL", "NUN 6040 LTL", "lettuce NUN 09094 LTL", "NUN 09094", "09094 LTL", "inbred NUN 09094 LTL" or "inbred variety NUN 09094 LTL" are used interchangeably herein and refer to a lettuce plant of NUN 09094 LTL, representative seed of which will be deposited under Accession No. NCIMB 43664.

A "seed of NUN 09094 LTL" refers to a seed of the inbred variety NUN 09094 LTL represented by the deposit with Accession No. NCIMB 43664. It can be grown into a plant of NUN 09094 LTL. A seed can be in any stage of maturity, for example, a mature, viable seed, or an immature, non-viable seed. A seed comprises an embryo and maternal tissues.

An "embryo of NUN 09094 LTL" refers to an embryo as present in a seed of the inbred variety NUN 09094 LTL, a representative sample of said seed of NUN 09094 LTL to be deposited under Accession No. NCIMB 43664.

A "seed grown on NUN 09094 LTL" refers to a seed grown on a mature plant of NUN 09094 LTL or inside a fruit of NUN 09094 LTL. The "seed grown on NUN 09094 LTL" contains tissues and DNA of the maternal parent, NUN 09094 LTL. The "seed grown on NUN 09094 LTL" contains an F1 embryo. When said seed is planted, it grows into a first generation progeny plant of NUN 09094 LTL. Since NUN 09094 LTL is an inbred and thus highly homozygous, the set of chromosomes inherited by the first generation progeny is predictable.

An "essentially homogeneous population of lettuce seed" is a population of seeds where at least 97%, 98%, 99% or more of the total population of seed are seed of NUN 09094 LTL.

An "essentially homogeneous population of lettuce plants" is a population of plants where at least 97%, 98%, 99% or more of the total population of plants are plants of NUN 09094 LTL.

The phrase "essentially free from other seed" refers to a population of seed where less than 3%, 2%, 1% or even less of the total population of seed is seed that is not a lettuce seed or, in another option, less than 3%, 2%, 1% or less of the total population of seed is seed that is not seed of NUN 09094 LTL.

"Tissue Culture" refers to a composition comprising isolated cells of the same or a different type or a collection of such cells organized into parts of a plant. Tissue culture of various tissues of lettuce and regeneration of plants is well known and widely published (see, e.g., Teng et al., HortScience. 1992, 27(9):1030-1032; Teng et al., HortScience. 1993, 28(6):669-1671; Zhang et al., Journal of Genetics and Breeding. 1992, 46(3):287-290). Similarly, methods of preparing cell cultures are known in the art.

"USDA descriptors" are the plant variety descriptors described for lettuce in the "Objective description of Variety—Lettuce (*Lactuca sativa* L.)", as published by U.S. Department of Agriculture, Agricultural Marketing Service, Science and Technology, Plant Variety Protection Office, Beltsville, Md. 20705 and which can be downloaded from the world wide web at ams.usda.gov/under sites/default/files/media/01-Lettuce %20 ST-470-01%202015.pdf and is hereby incorporated by reference in its entirety. "Non-USDA descriptors" are other descriptors suitable for describing lettuce.

"UPOV descriptors" are the plant variety descriptors described for lettuce in the "Guidelines for the Conduct of Tests for Distinctness, Uniformity and Stability," TG/013/11 (Geneva 2006, last updated May 4, 2017), as published by UPOV (International Union for the Protection of New Varieties and Plants) and which can be downloaded from the world wide web at upov.int/under edocs/tgdocs/en/tg013.pdf and is herein incorporated by reference in its entirety. Likewise, "UPOV methods" to determine specific parameters for the characterization of lettuce are described at upov.int.

"RHS" or "RHS color" refers to the color chart of the Royal Horticultural Society (UK), which publishes a botanical color chart quantitatively identifying colors by a defined numbering system. The chart may be purchased from Royal Horticulture Society Enterprise Ltd. RHS Garden; Wisley, Woking; Surrey GU236QB, UK, e.g., the RHS colour chart 2007.

"Plant part" includes any part of a plant, such as a plant organ, a plant cell, a plant protoplast, a plant cell tissue culture or a tissue culture from which a whole plant can be regenerated, a plant cell that is intact in a plant, a clone, a micropropagation, plant callus, a plant cell clump, a plant transplant, a vegetative propagation, a seedling, a fruit, a harvested fruit, a part of a fruit, a leaf, a part of a leaf, pollen, an ovule, an embryo, a petiole, a shoot or a part thereof, a stem or a part thereof, a root or a part thereof, a root tip, a cutting, a seed, a part of a seed, hypocotyl, cotyledon, a scion, a graft, a stock, a rootstock, a pistil, an anther, and a flower or parts of any of these and the like. Seed can be mature or immature. Pollen or ovules may be viable or non-viable. Also, any developmental stage is included, such as seedlings, cuttings prior or after rooting, mature plants or leaves. Alternatively, a plant part may also include a plant seed which comprises one or two sets of chromosomes derived from the parent plant (e.g., from NUN 09094 LTL). An F1 progeny produced from self-pollination of the inbred variety NUN 09094 LTL will thus comprise two sets of chromosomes derived from NUN 09094 LTL, while an F1 progeny derived from cross-fertilization of NUN 09094 LTL will comprise only one set of chromosomes from NUN 09094 LTL and the other set of chromosomes from the other parent.

"Reference variety" refers to variety Greenflash, a commercial variety from company Nunhems B.V., which has been planted in a trial together with NUN 09094 LTL. USDA descriptors of NUN 09094 LTL were compared to the USDA descriptors of their reference variety.

"Head" as used herein refers to lettuce heads, i.e., the plant without the root system, for example substantially all harvested leaves. Encompassed are immature leaves (e.g., "baby leaf") and mature leaves.

The "base" of a plant is the part of a lettuce plant where the leaves are attached to the root system of the plant.

"Core length" of the internal lettuce stem is measured from the base of the cut and trimmed head to the tip of the stem.

"Head weight" refers to the mean weight of saleable lettuce head, cut and trimmed to market specifications. "Head diameter" refers to the mean diameter of the cut and trimmed head, sliced vertically, and measured at the widest point perpendicular to the stem. "Head height" refers to the mean height of the cut and trimmed head, sliced vertically, and measured from the base of the cut stem to the leaf tip. "Core Length to Head Diameter Ratio (CLHD Ratio)" refers to the mean core length/head diameter ratio. It is calculated by dividing the mean core length with the mean head diameter. This is an indication of the head shape and of the ability of a lettuce plant to reduce the amount of surface which is on or close to the ground.

"Harvested plant material" refers herein to plant parts (e.g., leaves or heads detached from the whole plant) which have been collected for further storage and/or further use.

"Yield" means the total weight of all lettuce heads or leaves harvested per hectare of a particular line or variety. It is understood that "yield" expressed as weight of all lettuce heads or leaves harvested per hectare can be obtained by multiplying the number of plants per hectare times the "yield per plant". "Marketable yield" means the total weight of all marketable lettuce heads or leaves harvested per hectare of a particular line or variety, i.e., lettuce heads or leaves suitable for being sold for fresh consumption, having good color, glossiness size and texture and no or very low levels of deficiencies. A "marketable lettuce head or leaf" is a head or leaf that has commercial value.

A plant having "all the physiological and morphological characteristics" of a referred-to-plant means a plant showing the physiological and morphological characteristics of the referred-to-plant when grown under the same environmental conditions, preferably in the same experiment; the referred-to-plant can be a plant from which it was derived, e.g., the progenitor plant, the parent, the recurrent parent, the plant used for tissue- or cell culture, etc. A physiological or morphological characteristic can be a numerical characteristic or a non-numerical characteristic. In one aspect, a plant has "all but one, two or three of the physiological and morphological characteristics" of a referred-to-plant, or "all the physiological and morphological characteristics" of Table 1 and/or 2 or "all or all but one, two or three of the physiological and morphological characteristics" of Table 1 and/or 2.

The physiological and/or morphological characteristics mentioned above are commonly evaluated at significance levels of 1%, 5% or 10% if they are numerical, or for having an identical degree (or type) if not numerical, if measured under the same environmental conditions. For example, a progeny plant or a Single Locus Converted plant or a mutated plant of NUN 09094 LTL may have one or more (or all) of the essential physiological and/or morphological characteristics of said variety listed in Table 1 and/or 2, as determined at the 5% significance level (i.e., p<0.05) when grown under the same environmental conditions.

"Distinguishing characteristics" or "distinguishing morphological and/or physiological characteristics" refers herein to the characteristics which distinguish (i.e., are different) between the new variety and other lettuce varieties, such as the Reference Variety, when grown under the same environmental conditions. The distinguishing characteristics between NUN 09094 LTL and its Reference Variety are described elsewhere herein and also can be seen in Table 1 and/or Table 2. When comparing NUN 09094 LTL with different varieties, the distinguishing characteristics will be different. In one aspect, the distinguishing characteristics may therefore include at least one, two, three or more (or all) of the characteristics listed in Table 1 and/or 2. All numerical distinguishing characteristics are statistically significantly different at p<0.05 between NUN 09094 LTL and the other variety, e.g., the Reference Variety of NUN 09094 LTL.

NUN 09094 LTL has the following distinguishing characteristics when compared to the Reference Variety: 1) Average mature leaf length; 2) Average mature leaf width; 3) Typical mature leaf margin incision density; 4) Typical mature leaf margin indentation; 5) Typical mature leaf undulation of the apical margin; 6) Typical mature leaf blistering; 7) Typical mature leaf thickness; 8) Average mature plant spread of frame leaves; 9) Average core diameter at base of head; and 10) Ratio of frame leaves/core diameter. This can be seen in, for example, Table 1, where the USDA characteristics of NUN 09094 LTL are compared to the characteristics of the Reference Variety, when grown under the same environmental conditions A lettuce plant "comprising the distinguishing characteristics of NUN 09094 LTL" (such as a progeny plant) refers herein to a plant which does not differ significantly from said variety in the distinguishing characteristics above. Therefore, in one aspect, the disclosure provides a plant (such as a progeny plant of NUN 09094 LTL) which does not differ significantly from NUN 09094 LTL in the distinguishing characteristics above.

Similarity and differences between two different plant lines or varieties can be determined by comparing the number of morphological and/or physiological characteristics (e.g., the characteristics as listed in Table 1 and/or 2) that are the same (i.e., statistically not significantly different) or that are different (i.e., statistically significantly different) between the two plant lines or varieties when grown under the same environmental conditions. A numerical characteristic is considered to be "the same" when the value for a numeric characteristic is not significantly different at the 1% (p<0.01) or 5% (p<0.05) significance level, using one way Analysis of variance (ANOVA), a standard method known to the skilled person. Non-numerical or "degree" or "type" characteristic are considered "the same" when the values have the same "degree" or "type" when scored using USDA and/or UPOV descriptors, if the plants are grown under the same environmental conditions.

As used herein, the term "variety", "cultivated lettuce" or "cultivar" means a plant grouping within a single botanical taxon of the lowest known rank, which grouping, irrespective of whether the conditions for the grant of a breeder's right are fully met, can be defined by the expression of the characteristics resulting from a given genotype or combination of genotypes, distinguished from any other plant grouping by the expression of at least one of the said characteristics and considered as a unit with regard to its suitability for being propagated unchanged.

"Regeneration" refers to the development of a plant from cell culture or tissue culture or vegetative propagation.

"Vegetative propagation", "vegetative reproduction" or "clonal propagation" are used interchangeably herein and mean a method of taking a part of a plant and allowing that plant part to form at least roots, and optionally develop into a mature plant, and also refers to a plant or plantlet obtained by that method. Optionally, the vegetative propagation is grown into a mature plant. The skilled person is aware of what plant parts are suitable for use in the method.

"Crossing" refers to the mating of two parent plants. The term encompasses "cross-pollination" and "selfing". "Selfing" refers to self-pollination of a plant, i.e., the transfer of pollen from the anther to the stigma of the same plant. "Cross-pollination" refers to the fertilization by the union of two gametes from different plants.

As used herein, the terms "resistance" and "tolerance" are used interchangeably to describe plants that show no symptoms or significantly reduced symptoms to a specified biotic pest, pathogen, abiotic influence or environmental condition compared to a susceptible plant. These terms are optionally also used to describe plants showing some symptoms but that are still able to produce marketable product with an acceptable yield.

The term "traditional breeding techniques" encompasses herein crossing, selfing, selection, doubled haploid production, embryo rescue, protoplast fusion, marker assisted selection, mutation breeding etc. as known to the breeder (i.e., methods other than genetic modification/transformation/transgenic methods), by which, for example, a genetically heritable trait can be transferred from one lettuce line or variety to another. It optionally includes epigenetic modifications.

"Backcrossing" is a traditional breeding technique used to introduce a trait into a plant line or variety. The plant containing the trait is called the donor plant and the plant into which the trait is transferred is called the recurrent parent. An initial cross is made between the donor parent and the recurrent parent to produce a progeny plant. Progeny plants which have the trait are then crossed to the recurrent parent. After several generations of backcrossing and/or selfing the recurrent parent comprises the trait of the donor. The plant generated in this way may be referred to as a "single trait converted plant". The technique can also be used on a parental line of a hybrid.

"Progeny" as used herein refers to a plant obtained from a plant designated NUN 09094 LTL. A progeny may be obtained by regeneration of cell culture or tissue culture or parts of a plant of said variety; or selfing of a plant of said variety. In further aspects, progeny may also encompass plants obtained from crossing a one plant of NUN 09094 LTL with another lettuce plant of the same variety or another variety or line, or with wild lettuce plants. A progeny may comprise a mutation or a transgene. A first generation progeny is the progeny directly derived from, obtained from, obtainable from or derivable from the parent plant by, e.g., traditional breeding methods (selfing and/or crossing) or regeneration. Thus, a plant of NUN 09094 LTL is the male parent, the female parent or both of a first generation progeny of NUN 09094 LTL. Progeny may have all the physiological and morphological characteristics of NUN 09094 LTL, when grown under the same environmental conditions. Using common breeding methods such as backcrossing or recurrent selection, one or more specific characteristics may be introduced into said variety, to provide or a plant comprising all but 1, 2, or 3 or more of the morphological and physiological characteristics of NUN 09094 LTL (as listed in Table 1 and/or 2).

The terms "gene converted" or "conversion plant" or "single locus converted plant" in this context refer to lettuce plants which are developed by backcrossing wherein essentially all of the desired morphological and physiological characteristics of the parent variety or line are recovered, in addition to the one or more genes transferred into the parent via the backcrossing technique (optionally including reverse breeding or reverse synthesis of breeding lines) or via genetic engineering or through mutation breeding. Likewise, a "Single Locus Converted (Conversion) Plant" refers to plants developed by plant breeding techniques comprising or consisting of mutation and/or by genetic transformation and/or by backcrossing, wherein essentially all of the desired morphological and physiological characteristics of a lettuce variety are recovered in addition to the characteristics of the single locus having been transferred into the variety via the backcrossing technique. In case of a hybrid, the gene may be introduced in the male or female parental line.

"Marker" refers to a readily detectable phenotype, preferably inherited in codominant fashion (both alleles at a locus in a diploid heterozygote are readily detectable), with no environmental variance component, i.e., a heritability of 1.

"Average" refers herein to the arithmetic mean.

The term "mean" refers to the arithmetic mean of several measurements. The skilled person understands that the appearance of a plant depends to some extent on the growing conditions of said plant. Thus, the skilled person will know typical growing conditions for lettuces described herein. The mean, if not indicated otherwise within this application, refers to the arithmetic mean of measurements on at least 10 different, randomly selected plants of a variety or line.

DETAILED DESCRIPTION OF VARIOUS EMBODIMENTS OF THE INVENTION

The disclosure relates to a plant of NUN 09094 LTL wherein a representative sample of seeds of said variety will be deposited under the Budapest Treaty, with Accession No. NCIMB 43664. NUN 09094 LTL is a narrow oakleaf lettuce that can be grown as babyleaf, and is suitable for growing in the open field.

The disclosure also relates to a seed of a new lettuce variety described herein, referred to as NUN 09094 LTL, wherein a representative sample of said seed will be deposited under the Budapest Treaty, with Accession No. NCIMB 43664.

In another aspect, the disclosure provides for a plant part of NUN 09094 LTL, such as a head or a leaf, a representative sample of seed from said variety will be deposited under the Budapest Treaty, with Accession No. NCIMB 43664.

A seed of inbred variety NUN 09094 LTL is obtainable by selfing the variety and harvesting the seeds produced. The resultant seeds can be grown to produce plants of said variety. In one aspect, a seed or a plurality of seeds of said variety are packaged into a container of any size or type (e.g., bags, cartons, cans, etc.). The seed may be disinfected, primed and/or treated with various compounds, such as seed coatings or crop protection compounds. The seed produces a plant of NUN 09094 LTL.

The disclosure also provides a plant of lettuce NUN 09094 LTL, or a head or a leaf or other plant part thereof, produced from a seed, wherein a representative sample of said seeds will be deposited under the Budapest Treaty, with Accession No. NCIMB 43664.

The disclosure also provides a plant part obtained from NUN 09094 LTL, wherein said plant part is: a leaf, a part of a leaf, a head, a part of a head, a fruit, a part of a fruit, pollen, an ovule, a cell, a petiole, a shoot or a part thereof, a stem or a part thereof, a root or a part thereof, a root tip, a cutting, a seed, a part of a seed, seedcoat or another maternal tissue which is part of a seed grown on said variety, hypocotyl, cotyledon a pistil, an anther, or a flower or a part thereof. Heads and leaves are particularly important plant parts. In a further aspect, the plant part obtained from variety NUN 09094 LTL is a cell, optionally a cell in a cell or tissue culture. The cell may be grown into a plant of NUN 09094 LTL. A part of a variety described herein, i.e., NUN 09094 LTL (or of progeny NUN 09094 LTL or of a plant having all physiological and/or morphological characteristics but one, two or three which are different from those of NUN 09094 LTL) further encompasses any cells, tissues, organs obtainable from the seedlings or plants in any stage of maturity.

The disclosure also provides for a food or feed product or a processed product comprising or consisting of a plant part described herein. The plant part may be a lettuce head or leaf or part thereof and/or an extract from a leaf or another plant part described herein comprising at least one cell of NUN 09094 LTL. The food or feed product may be fresh or processed, e.g., dried, grinded, powdered, pickled, chopped, cooked, roasted, in a sauce, in a sandwich, pasted, puréed or concentrated, juiced, pickled, canned, steamed, boiled, fried, blanched and/or frozen, etc.

Such a plant part of NUN 09094 LTL can be stored and/or processed further. The disclosure thus also provides for a food or feed products comprising one or more of such parts, such as canned, chopped, cooked, roasted, in a sauce, in a sandwich, pasted, puréed or concentrated, juiced, frozen, dried, pickled, or powdered lettuce heads or leaves from NUN 09094 LTL or from progeny thereof, or from a derived variety, such as a plant having all but one, two or three physiological and/or morphological characteristics of NUN 09094 LTL.

In another aspect, the disclosure provides for a lettuce head or leaf of NUN 09094 LTL, or a part of a leaf of said variety. The head or leaf can be in any stage of maturity, such as immature or mature. In another aspect, the disclosure provides a container comprising a plurality of harvested lettuce heads or leaves or parts of lettuce heads or leaves of said variety, or lettuce heads or leaves of progeny thereof, or lettuce heads or leaves of a derived variety. Marketable lettuce heads or leaves are generally sorted by size and quality after harvest. Alternatively, the lettuce heads or leaves can be sorted by leaf size, shape, texture, glossiness or color.

In another aspect, the plant, plant part or seed of NUN 09094 LTL is inside a container. For example, the disclosure provides containers such as cans, boxes, crates, bags, cartons, Modified Atmosphere Packaging, films (e.g. biodegradable films), etc. comprising a plant or a part of a plant (fresh and/or processed, preferably a head or a leaf) of NUN 09094 LTL or a seed of NUN 09094 LTL. In a particular aspect, the container comprises a plurality of seeds of NUN 09094 LTL, or a plurality of plant parts of NUN 09094 LTL.

The disclosure further relates to a lettuce variety (e.g., NUN 09094 LTL), which—when compared to its Reference Variety Greenflash—has the following distinguishing characteristics: 1) Average mature leaf length; 2) Average mature leaf width; 3) Typical mature leaf margin incision density; 4) Typical mature leaf margin indentation; 5) Typical mature leaf undulation of the apical margin; 6) Typical mature leaf blistering; 7) Typical mature leaf thickness; 8) Average mature plant spread of frame leaves; 9) Average core diameter at base of head; and 10) Ratio of frame leaves/core diameter, where the characteristics are determined at the 5% significance level for plants grown under the same environmental conditions. Also encompassed by the disclosure are parts of that plant.

In one aspect, a plant of NUN 09094 LTL or a progeny plant thereof, comprises all of the following morphological and/or physiological characteristics (i.e., average values of distinguishing characteristics, as indicated on the USDA Objective description of variety—lettuce (unless indicated otherwise)): 1) Average mature leaf length; 2) Average mature leaf width; 3) Typical mature leaf margin incision density; 4) Typical mature leaf margin indentation; 5) Typical mature leaf undulation of the apical margin; 6) Typical mature leaf blistering; 7) Typical mature leaf thickness; 8) Average mature plant spread of frame leaves; 9) Average core diameter at base of head; and 10) Ratio of frame leaves/core diameter, where the characteristics are determined at the 5% significance level for plants grown under the same environmental conditions. An example of values for the distinguishing characteristics collected in a trial run according to UDSA requirements can be found in Table 1. A part of this plant is also provided.

In another aspect, NUN 09094 LTL has resistance to Downy mildew (*Bremia lactucae*) isolate B1: 1-33 that is 9 (present) and to *Nasonovia ribisnigri* that is 9 (present).

NUN 09094 LTL may further exhibit one or more of the following traits: a) Average plant height, b) Typical head size class, c) Average core height, d) Typical glossiness, and/or e) Average leaf length/width index.

The disclosure further provides a lettuce plant which does not differ from the plant of NUN 09094 LTL as determined at the 1%, 2%, 3%, 4% or 5% significance level when grown under the same environmental conditions. In a particular aspect, the plants are measured in the same trial (e.g., the trial is conducted as recommended by the USDA or UPOV). The disclosure also comprises a part of said plant, preferably a head or a leaf.

The disclosure also provides a tissue or cell culture comprising cells of NUN 09094 LTL. Such a tissue culture can, for example, be grown on plates or in liquid culture, or be frozen for long term storage. The cells of NUN 09094 LTL used to start the culture can be any plant part suitable for vegetative reproduction, or in a particular aspect can be one or more of an embryo, meristem, a cotyledon, a hypocotyl, pollen, a leaf, an anther, a root, a root tip, a pistil, a petiole, a flower, a fruit, seed, and/or a stem of NUN 09094 LTL. In another particular aspect, the tissue culture does not contain somaclonal variation or has reduced somaclonal variation. The skilled person is familiar with methods to reduce or prevent somaclonal variation, including regular reinitiation.

In one aspect, the disclosure provides a lettuce plant regenerated from the tissue or cell culture of NUN 09094 LTL, wherein the regenerated plant is not significantly different from NUN 09094 LTL in all, or all but one, two or three, of the physiological and morphological characteristics (determined at the 5% significance level when grown under the same environmental conditions). Optionally, the plant has one, two or three the physiological and morphological characteristics that are affected by a mutation or by transformation. In another aspect, the disclosure provides a lettuce plant regenerated from the tissue or cell culture of NUN 09094 LTL, wherein the plant has all of the physiological and morphological characteristics of said variety determined at the 5% significance level when grown under the same environmental conditions. In these cases, similarity or difference of a characteristic is determined by measuring the characteristics of a representative number of plants grown under the same environmental conditions, determining whether type/degree characteristics are the same or different and determining whether numerical characteristics are significantly different (determined at the 5% significance level).

A lettuce described herein, such as NUN 09094 LTL, or its progeny, or a plant having all physiological and/or morphological characteristics but one, two or three which are different from those of NUN 09094 LTL can also be reproduced using vegetative reproduction methods. Therefore, the disclosure provides for a method of producing a plant, or a part thereof, of NUN 09094 LTL, comprising vegetative propagation of said variety. Vegetative propagation comprises regenerating a whole plant from a plant part of NUN 09094 LTL (or from a progeny of said variety or from or a plant having all physiological and/or morphological characteristics of said variety but one, two or three different characteristics), such as a cutting, a cell culture or a tissue culture.

The disclosure also provides methods of vegetatively propagating a part of the plant of the disclosure NUN 09094 LTL. In certain aspects, the method comprises: (a) collecting tissue or cells capable of being propagated from a plant described herein; (b) cultivating said tissue or cells to obtain proliferated shoots; and (c) rooting said proliferated shoots, to obtain rooted plantlets. Steps (b) and (c) may also be reversed, i.e., first cultivating said tissue to obtain roots and then cultivating the tissue to obtain shoots, thereby obtaining rooted plantlets. The rooted plantlets may then be further grown, to obtain plants. In one aspect, the method further comprises step (d) growing plants from said rooted plantlets. Therefore, the method also comprises regenerating a whole plant from said part of NUN 09094 LTL.

In a particular aspect, the part of the plant to be propagated is a cutting, a cell culture or a tissue culture.

The disclosure also provides for a vegetatively propagated plant of NUN 09094 LTL (or from progeny of said variety or from or a plant having all but one, two or three physiological and/or morphological characteristics of NUN 09094 LTL), wherein the plant has all of the morphological and physiological characteristics of NUN 09094 LTL, when the characteristics are determined at the 5% significance level for plants grown under the same conditions. In another aspect, the propagated plant has all but one, two or three of the morphological and physiological characteristics of NUN 09094 LTL, when the characteristics are determined at the 5% significance level for plants grown under the same conditions. A part of said propagated plant or said propagated plant with one, two or three differences is also included.

In another aspect, the disclosure provides a method for producing a lettuce plant part, such as a head or a leaf, comprising growing a plant of NUN 09094 LTL until it develops at least one leaf, or develops a head, and collecting said leaf or head. In a particular aspect, the head or leaf is collected at harvest maturity. In another aspect, the leaf is collected at babyleaf stage. A plant of NUN 09094 LTL can be produced by seeding directly in the soil (e.g., field) or by germinating the seeds in controlled environment conditions (e.g., greenhouses) and then transplanting the seedlings into the field (see, e.g., Gonai et al., J. of Exp. Bot., 55(394): 111, 2004; http://anrcatalog.ucanr.edu/pdf/7215.pdf; http://an-rcatalog.ucanr.edu/pdf/7216.pdf). Lettuce may also be grown in tunnels. Moreover, said variety can be grown in hydroponic cultures as described in, e.g., US2008/0222949, which is herein incorporated by reference in its entirety, and the skilled person is familiar with various types of hydroponic cultures. Alternatively, seed of said plants described herein may be grown on peat block for use as root ball lettuce. Furthermore, plants described herein may be combined with 1, 2 or 3 other lettuce varieties to be grown as "composite lettuce" (see, e.g., EP1197137, which is herein incorporated by reference in its entirety).

In still another aspect, the disclosure provides a method of producing a lettuce plant, comprising crossing a plant of lettuce NUN 09094 LTL with a second lettuce plant at least once, allowing seed to develop and optionally harvesting said progeny seed. The skilled person can select progeny from said crossing. Optionally, the progeny is crossed twice, thrice, or four, five, six or seven times, and allowed to set seed. In one aspect, "crossing" comprises planting seeds of a first and a second parent lettuce plant, often in proximity so that pollination will occur; for example, mediated by insect vectors. Alternatively, pollen can be transferred manually. Where the plant is self-pollinated, pollination may occur without the need for direct human intervention other than plant cultivation. After pollination the plant can produce seed.

In another aspect, the disclosure provides a method of producing a plant, comprising selfing a plant of NUN 09094 LTL, and selecting a progeny plant from said selfing. In one aspect the progeny plant retains all or all but one, two or three the distinguishing characteristics of NUN 09094 LTL, described above when grown under the same environmental conditions. In a different aspect the progeny plant comprises all of the physiological and morphological characteristic of NUN 09094 LTL, of Table 1 and/or Table 2.

In other aspects, the disclosure provides a progeny plant of variety NUN 09094 LTL such as a progeny plant obtained by further breeding that variety. Further breeding with NUN 09094 LTL includes selfing that variety one or more times and/or cross-pollinating that variety with another lettuce plant or variety. In particular, the disclosure provides for a progeny plant that retains all the essential morphological and physiological characteristics of NUN 09094 LTL, or, in another aspect, a progeny plant that retains all, or all but one, two or three, of the morphological and physiological characteristics of NUN 09094 LTL, optionally all or all but one, two or three of the characteristics as listed in Table 1 and/or 2 for that variety, when grown under the same environmental conditions, determined at the 5% significance level for numerical characteristics. In a particular aspect, the progeny is a first generation progeny, i.e., the ovule or the pollen (or both) used in the crossing is an ovule or pollen of variety NUN 09094 LTL, i.e. the pollen comes from an anther of NUN 09094 LTL, and the ovule comes from an ovary of NUN 09094 LTL. In another aspect, the disclosure provides for a vegetative reproduction of the variety and a plant having all, or all but 1, 2, or 3 of the physiological and morphological characteristics of NUN 09094 LTL (e.g., as listed in Table 1 and/or 2).

The disclosure also provides a method for collecting pollen of NUN 09094 LTL, comprising growing a plant of NUN 09094 LTL until at least one flower contains pollen and collecting the pollen. Preferably, the pollen is collected when it is mature or ripe. A suitable method for collecting pollen comprises collecting anthers or the part of the anther that contains pollen, for example by cutting it off. Pollen can be collected in containers. Optionally, collected pollen can be used to pollinate a lettuce flower.

The morphological and/or physiological differences between two different individual plants of the disclosure (e.g., between NUN 09094 LTL and a progeny of NUN 09094 LTL) or between a plant of NUN 09094 LTL or progeny of said variety, or a plant having all, or all but 1, 2, or 3, of the physiological and morphological characteristics of NUN 09094 LTL (or all, or all but 1, 2, or 3 of the characteristics as listed in Table 1 and/or 2) and another known variety can easily be established by growing said variety next to each other or next to the other variety (in the same field, under the same environmental conditions), preferably in several locations which are suitable for said lettuce cultivation, and measuring morphological and/or physiological characteristics of a number of plants (e.g., to calculate an average value and to determine the variation range/uniformity within the variety). For example, trials can be carried out in Acampo Calif., USA (N 38 degrees 07'261"/W 121 degrees 18' 807", USA, whereby various characteristics, for example maturity, leaf shape, size and texture, leaf color and glossiness, bolt shape, surface and length, flower size and color, head weight, disease resistance, insect resistance and resistance to physiological stress can be measured and directly compared for species of lettuce. Thus, the disclosure comprises lettuce plant having one, two or three physiological and/or morphological characteristics which are different from those of the plant of NUN 09094 LTL and which otherwise has all the physiological and morphological characteristics of the plant of NUN 09094 LTL, when determined at the 5% significance level for plants grown under the same environmental conditions. In a particular aspect, the different characteristic is affected by a mutation, optionally induced mutation, or by transformation.

The morphological and physiological characteristics (and the distinguishing characteristics) of NUN 09094 LTL are provided in Table 1 and/or 2. The disclosure also provides a plant obtainable from NUN 09094 LTL (e.g., by selfing and/or crossing and/or backcrossing with said variety and/or progeny of said variety) comprising all or all but one, two or three of the physiological and morphological characteristics of NUN 09094 LTL, listed in Table 1 and/or 2 as determined at the 5% significance level for numerical characteristics or identical for non-numerical characteristics when grown under the same environmental conditions and/or comprising one or more (or all; or all except one, two or three) characteristics when grown under the same environmental conditions.

Also, at-harvest and/or post-harvest characteristics of heads or a leaves can be compared, such as cold storage holding quality, discoloration, and crunchiness.

The morphological and/or physiological characteristics may vary somewhat with variation in the environment (such as temperature, light intensity, day length, humidity, soil, fertilizer use), which is why a comparison under the same environmental conditions is preferred. Colors can best be measured using the Royal Horticultural Society (RHS) Chart.

In yet a further aspect, the disclosure provides for a method of producing a new lettuce plant. The method comprises crossing a plant of the disclosure, e.g., NUN 09094 LTL, or a plant comprising all but 1, 2, or 3 of the morphological and physiological characteristics of said variety (as listed in Table 1 and/or 2), or a progeny plant thereof, either as male or as female parent, with a second lettuce plant (or a wild relative of lettuce) one or more times, and/or selfing a lettuce plant described herein (e.g., NUN 09094 LTL), or a progeny plant thereof, one or more times, and selecting progeny from said crossing and/or selfing. The second lettuce plant may for example be a line or variety of the species Lactuca sativa or even other Lactuca species.

The disclosure provides for methods of producing plants which retain all the morphological and physiological characteristics of a plant of the disclosure (e.g., NUN 09094 LTL). The disclosure provides also for methods of producing a plant comprising all but 1, 2, or 3 or more of the morphological and physiological characteristics of NUN 09094 LTL, (e.g. as listed in Table 1 and/or 2), but which are still genetically closely related to said variety. The relatedness can, for example be determined by fingerprinting techniques (e.g., making use of isozyme markers and/or molecular markers such as Single-nucleotide polymorphism (SNP) markers, amplified fragment length polymorphism (AFLP) markers, microsatellites, minisatellites, Random Amplified Polymorphic DNA (RAPD) markers, restriction fragment length polymorphism (RFLP) markers and others). A plant is "closely related" to NUN 09094 LTL, if its DNA fingerprint is at least 80%, 90%, 95% or 98% identical to the fingerprint of NUN 09094 LTL. In a particular aspect, AFLP markers are used for DNA fingerprinting (Vos et al. 1995, Nucleic Acid Research 23: 4407-4414). A closely related plant may have a Jaccard's Similarity index of at least about 0.8, preferably at least about 0.9, 0.95, 0.98 or more.

The disclosure also provides a plant and a variety obtained or selected by applying these methods on NUN 09094 LTL. Such a plant may be produced by crossing and/or selfing, or alternatively, a plant may simply be identified and selected amongst plants of said variety, or progeny of said variety, e.g., by identifying a variant within NUN 09094 LTL or within progeny of said variety (e.g., produced by selfing) which variant differs from NUN 09094 LTL, in one, two or three of the morphological and/or physiological characteristics (e.g. in one, two or three distinguishing characteristics), e.g., those listed in Table 1 and/or 2 or others. In one aspect the disclosure provides a lettuce plant having a Jaccard's Similarity index with NUN 09094 LTL, of at least 0.8, e.g. at least 0.85, 0.9, 0.95, 0.98 or even at least 0.99.

In some aspects, the disclosure provides a lettuce plant comprising genomic DNA having at least 95%, 96%, 97%, 98% or 99% sequence identity compared to the genomic DNA sequence of a plant of NUN 09094 LTL as deposited under Accession Number NCIMB. In some aspects, the lettuce plant further comprises all or all but 1, 2, or 3 of the morphological and physiological characteristics of NUN 09094 LTL (e.g., as listed in Table 1 and/or 2). In other aspects, the lettuce plant is a hybrid or other derived from a seed or plant of NUN 09094 LTL. In other aspects, the lettuce plant comprises the distinguishing characteristics of NUN 09094 LTL.

For the purpose of this disclosure, the "sequence identity" of nucleotide sequences, expressed as a percentage, refers to the number of positions in the two optimally aligned sequences which have identical residues (×100) divided by the number of positions compared. A gap, i.e., a position in the pairwise alignment where a residue is present in one sequence but not in the other, is regarded as a position with non-identical residues. A pairwise global sequence alignment of two nucleotide sequences is found by aligning the two sequences over the entire length according to the Needleman and Wunsch global alignment algorithm described in Needleman and Wunsch, 1970, J. Mol. Biol. 48(3):443-53). A full implementation of the Needleman- Wunsch global alignment algorithm is found in the needle program in The European Molecular Biology Open Software Suite (EMBOSS, Rice et al., Trends in Genetics June 2000, vol. 16, No. 6. pp. 276-277).

The description also provides methods for determining the identity of parental lines of plants described herein, in particular the identity of the female line. WO2013/182646, which is herein incorporated by reference, relates to a non-destructive method for analyzing maternal DNA of a seed. In this method, the DNA is dislodged from the seed coat surface and can be used to collect information on the genome of the maternal parent of the seed. This method for analyzing maternal DNA of a seed comprises contacting a seed with a fluid to dislodge DNA from the seed coat surface, and analyzing the DNA thus dislodged from the seed coat surface using methods known in the art. The skilled person is thus able to determine whether a seed has grown on a plant of NUN 09094 LTL or is a progeny of said variety, because the seed coat of the seed is a maternal tissue genetically identical to NUN 09094 LTL. In one aspect, the disclosure relates to a seed coat comprising maternal tissue of NUN 09094 LTL. In another aspect, the disclosure relates to a lettuce seed comprising maternal tissue of NUN 09094 LTL. Since NUN 09094 LTL is an inbred variety, with a very high degree of homozygosity, any F1 progeny will inherit the same, predictable, set of chromosomes from its parent. Thus, the skilled person will also be able to identify maternal tissues of a seed grown on a F1 progeny of NUN 09094 LTL, using the methods described in WO2013/182646. In another particular aspect, the skilled person can determine the identity of the female parental line of NUN 09094 LTL by analyzing the seed coat of a seed of that variety, In another aspect, the skilled person can determine whether a seed is grown on NUN 09094 LTL.

By crossing and/or selfing, (one or more) single traits may be introduced into NUN 09094 LTL (e.g., using backcrossing breeding schemes), while retaining the remaining morphological and physiological characteristics of said variety and/or retaining one or more or all distinguishing characteristics. A single trait converted plant may thereby be produced. For example, disease resistance genes may be introduced, genes responsible for one or more quality traits, yield, etc. Both single genes (e.g. dominant or recessive) and one or more QTLs (quantitative trait loci) may be transferred into NUN 09094 LTL by breeding with said variety.

Any pest or disease resistance genes may be introduced into a plant described herein, i.e. NUN 09094 LTL, progeny of said variety or into a plant comprising all but 1, 2, or 3 or more of the morphological and physiological characteristics of NUN 09094 LTL (e.g., as listed in Table 1). Resistance to one or more of the following diseases or pests may be introduced into plants described herein: Downy mildew, Powdery mildew, *Sclerotinia* rot, *Sclerotinia* drop, *Botrytis* (Grey Mold), *Verticillium* Wilt, *Pseudomonas* spp. (Bacterial Soft Rot), Bacterial Leaf Spot, Anthracnose, Bottom rot, Corky root rot, Lettuce mosaic virus, Turnip mosaic virus, Tomato bushy stunt virus (Dieback), Big vein, Cabbage Loopers, Root Aphid, Green Peach Aphid, Lettuce aphid, Pea leafminer, Beet western yellows and aster yellows. Other resistance genes, against pathogenic viruses (e.g., Lettuce infectious yellows virus (LIYV), lettuce mosaic virus (LMV), Cucumber mosaic virus (CMV), Beet western yellows virus (BWYV), Alfalfa mosaic virus (AMV)), fungi, bacteria, nematodes, insects or other pests. In one aspect, resistance against *Nasonovia ribisnigri* biotype Nr:0 and/or Nr:1 is introduced in a plant disclosed herein. Also, any resistances to physiological stresses may be introduced into a plant described herein, or progeny thereof or into a plant comprising all but 1, 2, or 3 or more of the morphological and physiological characteristics of said plant (e.g., as listed in Table 1 and/or 2). Resistance against one or more of the following is may be introduced into plants of the disclosure: Tipburn, Heat, Drought, Cold, Salt and/or Brown rob (Rib discoloration/rib blight).

The disclosure also provides a method for developing a lettuce plant in a lettuce breeding program, using NUN 09094 LTL, or its parts or progeny, as a source of plant breeding material. Suitable plant breeding techniques include recurrent selection, backcrossing, pedigree breeding, mass selection, mutation breeding and/or genetic marker enhanced selection. For example, in one aspect, the method comprises crossing NUN 09094 LTL or its progeny, or a plant comprising all but 1, 2, or 3 or more of the morphological and physiological characteristics of NUN 09094 LTL (e.g., as listed in Table 1 and/or 2), with a different lettuce plant, wherein one or more offspring of the crossing are subject to one or more plant breeding techniques: recurrent selection, backcrossing, pedigree breeding, mass selection, mutation breeding and genetic marker enhanced selection (see e.g., Brotman et al., Theor Appl Genet (2002) 104:1055-1063). Pedigree selection, also known as the "Vilmorin system of selection," is described in, e.g., Allard, 1960, John Wiley & Sons, Inc.: Principles of plant breeding: 119-128, Library of Congress Catalog Card Number: 60-14240. For breeding methods in general, see Principles of Plant Genetics and Breeding, 2007, George Acquaah, Blackwell Publishing, ISBN-13: 978-1-4051-3646-4.

A single trait converted plant or single locus converted plant of NUN 09094 LTL may be produced by (i) genetically transforming or mutating cells of NUN 09094 LTL; (ii) growing the cells into a plant; and (iii) optionally selecting a plant that contains the desired single locus conversion. The skilled person is familiar with various techniques for genetically transforming a single locus in a plant cell, or mutating said cell.

In another aspect, the disclosure provides a method of introducing a single locus conversion or introducing a desired trait into NUN 09094 LTL, comprising:
(a) crossing NUN 09094 LTL, representative seed of which to be deposited under Accession No. NCIMB 43664, with a second plant comprising a desired single locus to produce F1 progeny plants and obtaining progeny of said crossing; wherein the single locus comprised by the second plant is the locus to be introduced in the first plant;
(b) optionally selfing said F1 progeny plant to produce an F2 progeny plant having said single locus;
This method may be followed by:
(a) crossing the progeny plant with NUN 09094 LTL, representative seed of which to be deposited under Accession No. NCIMB 43664, and obtaining progeny of said cross; and
(b) optionally repeating step (c) one or more times in succession to produce selected second or higher backcross progeny plants that comprise the single locus and otherwise comprise essentially all physiological and morphological characteristics when grown under the same environmental conditions of NUN 09094 LTL.

The disclosure is also directed to a lettuce plant obtained from step a), b), c) or d) of the above method.

Any trait can be introduced. In one aspect, the trait to be used in the above method for single locus conversion is disease resistance and the resistance is conferred to any race of *Nasonovia ribisnigri*, any race of Downy mildew, Powdery mildew, *Sclerotinia* rot, *Sclerotinia* drop, *Botrytis* (Grey Mold), *Verticillium* Wilt, *Pseudomonas* spp. (Bacterial Soft Rot), Bacterial Leaf Spot, Anthracnose, Bottom rot, Corky root rot, Lettuce mosaic virus, Turnip mosaic virus, Tomato bushy stunt virus (Dieback), Big vein, Cabbage Loopers, Root Aphid, Green Peach Aphid, Lettuce aphid, Pea leafminer, Beet western yellows and aster yellows, *Sclerotinia minor* (leaf drop), *Sclerotinia sclerotiorum* (leaf drop), *Rhizoctonia solani* (bottom drop), *Erysiphe cichoracearum* (powdery mildew), *Fusarium oxysporum* f. sp. *lactucae* (*Fusarium* wilt), lettuce infectious yellows virus (LIYV), lettuce mosaic virus (LMV), Cucumber mosaic virus (CMV), Beet western yellows virus (BWYV), and/or Alfalfa mosaic virus (AMV).

The disclosure also provides a lettuce plant comprising at least a first set of the chromosomes of lettuce variety NUN 09094 LTL, a sample of seed of said variety will be deposited under Accession No. NCIMB 43664; optionally further comprising a single locus conversion or a mutation, conferring a desired trait. In another aspect, the desired trait is yield, storage properties, color, male sterility, herbicide tolerance, insect resistance, pest resistance, disease resistance, environmental stress tolerance, modified carbohydrate metabolism and/or modified protein metabolism.

In one aspect, a plant described herein (e.g., NUN 09094 LTL) may also be mutated (by e.g., irradiation, chemical mutagenesis, heat treatment, etc.) and mutated seeds or plants may be selected in order to change one or more characteristics of said variety. Methods such as TILLING may be applied to lettuce populations in order to identify mutants. Similarly, NUN 09094 LTL may be transformed and regenerated, whereby one or more chimeric genes are introduced into the variety or into a plant comprising all but 1, 2, 3, or more of the morphological and physiological characteristics (e.g., as listed in Table 1 and/or 2). Transformation can be carried out using standard methods, such as *Agrobacterium tumefaciens* mediated transformation or biolistics, followed by selection of the transformed cells and regeneration into plants. A desired trait (e.g., gene(s) conferring pest or disease resistance, herbicide, fungicide or insecticide tolerance, etc.) can be introduced into NUN 09094 LTL, or progeny of said variety, by transforming said variety or progeny of said variety with a transgene that confers the desired trait, wherein the transformed plant retains all or all but one, two or three of the phenotypic and/or morphological and/or physiological characteristics of NUN 09094 LTL, or the progeny of said variety and contains the desired trait.

The disclosure also provides a plant or a cell of a plant comprising a desired trait produced by mutating a plant of NUN 09094 LTL or a cell thereof and selecting a plant the desired trait, wherein the mutated plant retains all or all but one of the phenotypic and morphological characteristics of said variety, optionally as described for each variety in in Table 1 and/or 2, and contains the desired trait and wherein a representative sample of seed of NUN 09094 LTL, will be deposited under Accession No. NCIMB 43664. In a further aspect, the desired trait is yield, nutritional value, taste, color, crunchiness, male sterility, herbicide tolerance, insect resistance, pest resistance, disease resistance, environmental stress tolerance, modified carbohydrate metabolism and/or modified protein metabolism.

A suitable method for inducing mutation in NUN 09094 LTL comprises:

a. exposing a seed, a plant or a plant part or a cell of NUN 09094 LTL to a mutagenic compound or to radiation, wherein a representative sample of seed of NUN 09094 LTL is deposited under Accession Number NCIMB 43664;

b. selecting a seed, a plant or a plant part or a cell of NUN 09094 LTL having a mutation; and c. optionally growing and/or multiplying the seed, plant or plant part or cell of NUN 09094 LTL having the mutation.

The disclosure also provides a plant having one, two or three physiological and/or morphological characteristics which are different from those of NUN 09094 LTL, and which otherwise has all the physiological and morphological characteristics of said variety, wherein a representative sample of seed, will be deposited under Accession Number NCIMB 43664. In particular, variants which differ from NUN 09094 LTL, in none, one, two or three of the characteristics mentioned in Table 1 and/or 2 are encompassed.

A part of NUN 09094 LTL (or of progeny of said varieties or of a plant having all physiological and/or morphological characteristics but one, two or three which are different from those of said variety) encompasses any cells, tissues, organs obtainable from the seedlings or plants, such as but not limited to: a lettuce leaf or a part thereof, a cutting, hypocotyl, cotyledon, seed coat, pollen and the like. Such parts can be stored and/or processed further. The disclosure further provides for food or feed products comprising a part of NUN 09094 LTL or a part of progeny of said varieties, or a part of a plant having all but one, two or three physiological and/or morphological characteristics of NUN 09094 LTL, comprising one or more of such parts, optionally processed (such as canned, chopped, cooked, roasted, in a sauce, in a sandwich, pasted, puréed or concentrated, juiced, frozen, dried, pickled, or powdered).

In one aspect, a haploid plant and/or a doubled haploid plant of NUN 09094 LTL, or of a plant having all but one, two or three physiological and/or morphological characteristics of NUN 09094 LTL, or progeny of any of these, is encompassed herein. Haploid and doubled haploid (DH) plants can, for example, be produced by cell or tissue culture and chromosome doubling agents and regeneration into a whole plant. For DH production chromosome doubling may be induced using known methods, such as colchicine treatment or the like. In one aspect, the method comprises inducing a cell or tissue culture with a chromosome doubling agent, and regenerating the cells or tissues into a whole plant.

Also provided is a plant part obtainable from NUN 09094 LTL or from progeny of said variety or from a plant having all but one, two or three physiological and/or morphological characteristics which are different from those of NUN 09094 LTL, or from a vegetatively propagated plant of NUN 09094 LTL (or from its progeny or from a plant having all or all but one, two or three physiological and/or morphological characteristics which are different from those of NUN 09094 LTL), wherein the plant part is a leaf, a harvested leaf, a part of a leaf, a head, a harvested head, a part of a head, a fruit, a harvested fruit, a part of a fruit, pollen, an ovule, a cell, a petiole, a shoot or a part thereof, a stem or a part thereof, a root or a part thereof, a root tip, a cutting, a seed, a part of a seed, seed-coat or another maternal tissue which is part of a seed grown on NUN 09094 LTL, or hypocotyl, cotyledon, a pistil, an anther, and a flower or a part thereof.

In still yet another aspect, the disclosure provides a method of determining the genotype of a plant of the disclosure comprising detecting in the genome (e.g., a sample of nucleic acids) of the plant at least a first polymorphism or an allele. The skilled person is familiar with many suitable methods of genotyping, detecting a polymorphism or detecting an allele including restriction fragment length polymorphism identification (RFLP) of genomic DNA, random amplified polymorphic detection (RAPD) of genomic DNA, amplified fragment length polymorphism detection (AFLP), polymerase chain reaction (PCR), DNA sequencing, allele specific oligonucleotide (ASO) probes, and hybridization to DNA microarrays or beads. Alternatively, the entire genome could be sequenced. The method may, in certain aspects, comprise detecting a plurality of polymorphisms in the genome of the plant, for example by obtaining a sample of nucleic acid from a plant and detecting in said nucleic acids a plurality of polymorphisms. The method may further comprise storing the results of detecting the plurality of polymorphisms on a computer readable medium.

All documents (e.g., patent publications) are herein incorporated by reference in their entirety, including the following cited references:

"Objective description of Variety—Lettuce (*Lactuca sativa* L.)", U.S. Department of Agriculture, Agricultural Marketing Service, Plant Variety Protection Office, Beltsville, Md. 20705, world wide web at ams.usda.gov/.

"Guidelines for the Conduct of Tests for Distinctness, Uniformity and Stability," TG/013/10 (Geneva 2006, last updated May 4, 2017), UPOV the world wide web at upov.int/.

Acquaah, Principles of Plant Genetics and Breeding, 2007, Blackwell Publishing, ISBN-13: 978-1-4051-3646-4.

Allard, 1960, John Wiley & Sons, Inc.: Principles of plant breeding: 119-128, Library of Congress Catalog Card Number: 60-14240.

Brotman et al., Theor Appl Genet (2002) 104:1055-1063

Clewer, A. G., and D. H. Scarisbrick. 2001 contains a comprehensive explanation of the whole comparison process).

Gonai et al., J. of Exp. Bot., 55(394): 111, 2004

Teng et al., HortScience. 1992, 27(9): 1030-1032

Teng et al., HortScience. 1993, 28(6): 669-1671,

Zhang et al., Journal of Genetics and Breeding. 1992, 46(3): 287-290).

EP1197137

US2008/0222949

WO2013/182646

EXAMPLES

Development of NUN 09094 LTL

The inbred variety NUN 09094 LTL was developed from an initial cross between lettuce lines. The female and male ancestors were crossed to produce seeds. After the cross, progeny were self-pollinated or backcrossed, followed by pedigree selection and line selection. NUN 09094 LTL can be propagated by seeds or vegetatively, or by regeneration of a tissue culture. The seeds of NUN 09094 LTL can be grown to produce inbred plants and parts thereof (e.g. lettuce heads and leaves).

The Applicant concluded that NUN 09094 LTL is uniform and stable. This has been established through evaluation of horticultural characteristics. Several seed production events resulted in no observable deviation in genetic stability.

Deposit Information

A total of 2500 seeds of variety NUN 09094 LTL have been deposited according to the Budapest Treaty by Nunhems B.V. on Sep. 14, 2020 at the NCIMB Ltd., Ferguson Building, Craibstone Estate, Bucksburn, Aberdeen AB21 9YA, United Kingdom (NCIMB). The deposit has been assigned NCIMB 43664. A deposit of NUN 09094 LTL is also maintained at Nunhems B.V.

Access to the deposits will be available during the pendency of this application to persons determined by the Director of the U.S. Patent Office to be entitled thereto upon request. Subject to 37 C.F.R. § 1.808(b), all restrictions imposed by the depositor on the availability to the public of the deposited material will be irrevocably removed upon the granting of the patent. The deposit will be maintained for a period of 30 years, or 5 years after the most recent request, or for the enforceable life of the patent whichever is longer, and will be replaced if it ever becomes nonviable during that period. Applicant does not waive any rights granted under this patent on this application or under the Plant Variety Protection Act (7 U.S.C. § 2321 et seq.).

Table 1 and 2 show a comparison between NUN 09094 LTL and its Reference variety based on a trial in the USA. Table 1 lists the USDA descriptors of NUN 09094 LTL and its Reference variety. The most similar variety to NUN 09094 LTL is referred to as the Reference variety, a variety from Nunhems B.V., with the commercial name Greenflash. Two replications of 50 plants of each variety, from which at least 15 plants or plant parts were randomly selected, and were used to measure characteristics. For numerical characteristics, averages were calculated. For non-numerical characteristics, the type/degree were determined. Trial location Salinas, Calif. (36.11842 N; 121.014181 W).

TABLE 1

Objective description of NUN 09094 LTL and Reference variety Greenflash.

| USDA Descriptor | NUN 09094 LTL | Greenflash |
|---|---|---|
| Plant type: 1 = Cutting/Leaf; 2 = Butterhead; 3 = Bibb; 4 = Cos or Romaine; 5 = Great Lakes Group; 6 = Vanguard Group; 7 = Salinas Group; 8 = Eastern (Ithaca) Group; 9 = Stem; 10 = Latin; 11 = Other (__) Mature leaves (harvest mature outer leaves): Margin: | 1 | 1 |
| Incision depth (deepest penetration of margin): 1 = absent/shallow (Dark Green Boston), 2 = moderate (Vanguard), 3 = deep (Great Lakes 659) | 3 | 3 |
| Incision density: 3 = sparse, 5 = medium, 7 = dense, 9 = very dense | 5 | 7 |
| Indentation (finest divisions of the margin): 1 = entire, 2 = shallowly dentate (Great Lake 65), 3 = deeply dentate (Great Lake 659); 4 = Crenate (Vanguard); 5 = Other (Specify) | 2 | 4 |

TABLE 1-continued

Objective description of NUN 09094 LTL and Reference variety Greenflash.

| USDA Descriptor | NUN 09094 LTL | Greenflash |
|---|---|---|
| Undulations of the apical margin: 1 = absent/slight (Dark Green Boston), 2 = moderate (Vanguard), 3 = strong (Great Lakes 659) | 2 | 3 |
| Green color: 1 = very light green, 2 = light green, 3 = medium green, 4 = dark green; 5 = Very Dark Green; 6 = other | 3 (RHS 146A) | 3 (RHS 137A) |
| Anthocyanin: | | |
| Distribution: 1 = absent; 2 = Margin Only (Big Boston); 3 = spotted (California Cream Butter); 4 = throughout (Prize Head); 5 = Other (_) | 1 | 1 |
| Concentration: 1 = light, 2 = moderate, 3 = intense | NA | NA |
| Size: 1 = small, 2 = medium, 3 = large | 2 | 1 |
| Glossiness: 1 = dull, 2 = moderate, 3 = glossy | ½ | 2 |
| Blistering: 1 = absent/slight, 2 = moderate, 3 = strong | 1 | ½ |
| Leaf thickness: 1 = thin, 2 = intermediate, 3 = thick | 1 | 2 |
| Trichomes; 1 = absent, 2 = present | 1 | 1 |
| Plant | | |
| Spread of frame leaves (cm) | 8.76 | 9.92 |
| Head diameter (market trimmed with single cap leaf) | NA | NA |
| Head shape: 1 = flattened, 2 = Slightly Flattened; 3 = Spherical; 4 = elongate, 5 = non-heading; 6 = other (_) | 5 | 5 |
| Head size class: 1 = small, 2 = medium, 3 = large | 2 | 1 |
| Head per carton | NA | NA |
| Head weight (gram) | 14.5 | 15.3 |
| Head firmness: 1 = loose, 2 = Moderate; 3 = Firm, 4 = very firm | 1 | 1 |
| Butt | | |
| Shape: 1 = slightly concave, 2 = flat, 3 = rounded; 4 = V-shaped | 4 | 4 |
| Midrib: 1 = Flattened, 2 = Moderately Raised, 3 = prominently raised | NA | NA |
| Core | | |
| Diameter at base of head (mm) | 6.61 | 4.95 |
| Ratio of head spread (frame leaves)/core diameter | 2 | 1.39 |
| Core height from base of head to apex (mm) | 7.15 | 6.27 |
| Maturity (earliness of harvest-mature head formation) | | |
| Spring (days) | 37 days | |
| Adaptation: | | |
| Primary regions of adaptation | West Coast | West Coast |
| Season: 0 = not tested, 1 = not adapted, 2 = adapted | 2, all seasons | 2, all seasons |
| Greenhouse: 0 = not tested, 1 = not adapted, 2 = adapted | 0 | 0 |
| Soil type: 1 = mineral, 2 = organic, 3 = both | 3 | 3 |

TABLE 2

Other characteristics of variety NUN 09094 LTL and Reference Variety Greenflash

| Non-USDA Descriptor | NUN 09094 LTL | Greenflash |
|---|---|---|
| Leaf length in mm (harvest mature) | 142.16 | 97.13 |
| Leaf width in mm (harvest mature) | 81.53 | 89.69 |
| Leaf length/width ratio (harvest mature) | 17.44 | 10.83 |
| Plant height in cm (harvest mature) | 13.55 | 8.73 |

Table 1 and 2 contain typical values. Values may vary due to environment. Other values that are substantially equivalent are also within the scope of the disclosure. N.A.=not applicable; n.r.=not recorded.

The invention claimed is:

1. A plant, plant part, or seed of lettuce variety NUN 09094 LTL, wherein a representative sample of seed of said variety is deposited under Accession No. NCIMB 43664.

2. The plant part of claim 1, wherein the plant part is a leaf, a head, a pollen, an ovule, a fruit, a cutting, a flower, or a cell.

3. A seed that produces the plant of claim 1.

4. A seed grown on the plant of claim 1.

5. A lettuce plant or a part thereof having all of the physiological and morphological characteristics of the plant of claim 1.

6. A tissue or cell culture comprising a cell of the plant of claim 1.

7. The tissue or cell culture according to claim 6, comprising cells or protoplasts derived from a plant part suitable for vegetative reproduction.

8. The tissue or cell culture according to claim 6, wherein the plant part is an embryo, a meristem, a cotyledon, a hypocotyl, a pollen, a leaf, an anther, a root, a root tip, a pistil, a petiole, a flower, a fruit, a seed, or a stem.

9. A lettuce plant regenerated from the tissue or cell culture of claim 6, wherein the plant has all of the physiological and morphological characteristics of the plant of lettuce variety NUN 09094 LTL, when grown under the same environmental conditions, and wherein a representative sample of seed of lettuce variety NUN 09094 LTL is deposited under Accession No. NCIMB 43664.

10. A method of producing the plant of claim 1, said method comprising vegetative propagation of at least a part of the plant of variety NUN 09094 LTL, wherein a representative sample of seed of said variety is deposited under Accession No. NCIMB 43664.

11. The method of claim 10, wherein said vegetative propagating comprises regenerating a whole plant from said part of the plant of variety NUN 09094 LTL, wherein a representative sample of seed of said variety is deposited under Accession No. NCIMB 43664.

12. The method of claim 10, wherein said part is a cutting, a cell culture or a tissue culture.

13. A vegetative propagated plant of claim 1, or a part thereof, wherein die vegetative propagated plant or part thereof has all of the physiological and morphological characteristics of the plant of lettuce variety NUN 09094 LTL, when grown under the same environmental conditions, and wherein a representative sample of seed of lettuce variety NUN 09094 LTL is deposited under Accession No. NCIMB 43664.

14. A method of producing a lettuce plant, said method comprising crossing the plant of claim 1 with a second lettuce plant at least once, selecting a progeny lettuce plant from said crossing and allowing the progeny lettuce plant to form seed.

15. A first generation progeny plant of the plant of claim 1 obtained by crossing the plant of lettuce variety NUN 09094 LTL with itself or with another plant.

16. A lettuce plant having all the physiological and morphological characteristics of lettuce variety NUN 09094 LTL, when grown under the same environmental conditions, and wherein a representative sample of seed of said lettuce variety is deposited under Accession No. NCIMB 43664, further comprising a transgene.

17. A method of making doubled haploid of lettuce variety NUN 09094 LTL, said method comprising making doubled haploid cells from haploid cells from the plant, plant part, or seed of claim 1 by chromosome doubling, wherein a representative sample of seed of lettuce variety NUN 09094 LTL is deposited under Accession No. NCIMB 43664.

18. A container comprising the plant, plant part or seed of claim 1.

19. A food, a feed product, or a processed product comprising the plant part of claim 2.

20. A method of producing a lettuce head or a lettuce leaf, said method comprising growing the plant of claim 1 until it develops at least one leaf or a head, and collecting the leaf or head.

21. A method for inducing mutation in the plant of claim 1, comprising:
　a. exposing the seed, plant, or plant part of lettuce variety NUN 09094 LTL to a mutagenic compound or to radiation, wherein a representative sample of seed of lettuce variety NUN 09094 LTL is deposited under Accession No. NCIMB 43664; and
　b. selecting the seed, plant, a plant part, or cell of lettuce variety NUN 09094 LTL having a mutation.

22. A method for collecting pollen of lettuce variety NUN 09094 LTL, said method comprising growing a plant of claim 1 until at least one flower contains pollen and collecting the pollen.

23. A method of producing a modified lettuce plant, wherein the method comprises mutating a lettuce plant or plant part of lettuce variety NUN 09094 LTL, wherein a representative sample of seed of lettuce variety NUN 09094 LTL is deposited under Accession No. NCIMB 43664.

24. A lettuce plant grown from the seed of claim 4.

25. A plant of lettuce variety NUN 09094 LTL further comprising a transgene conferring a desired trait and otherwise has all of the physiological and morphological characteristics of the plant of claim 1 when grown under the same environmental conditions, wherein a representative sample of seed of said lettuce variety is deposited under Accession Number NCIMB 43664, wherein the desired trait is yield, storage properties, color, male sterility, herbicide tolerance, insect tolerance, insect resistance, pest resistance, disease resistance, environmental stress tolerance, modified carbohydrate metabolism, or modified protein metabolism.

26. A seed that produces the plant of claim 5.

* * * * *

UNITED STATES PATENT AND TRADEMARK OFFICE
CERTIFICATE OF CORRECTION

PATENT NO. : 10,834,884 B2
APPLICATION NO. : 16/003890
DATED : November 17, 2020
INVENTOR(S) : Johan Van Zee Page 1 of 1

It is certified that error appears in the above-identified patent and that said Letters Patent is hereby corrected as shown below:

In the Claims

In Claim 13, Column 23, Line 9, replace "die" with --the--

Signed and Sealed this
Nineteenth Day of January, 2021

Andrei Iancu
*Director of the United States Patent and Trademark Office*